(12) United States Patent
Gregorich et al.

(10) Patent No.: US 7,344,560 B2
(45) Date of Patent: Mar. 18, 2008

(54) MEDICAL DEVICES AND METHODS OF MAKING THE SAME

(75) Inventors: Daniel J. Gregorich, Mound, MN (US); Jonathan S. Stinson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 433 days.

(21) Appl. No.: 10/961,289

(22) Filed: Oct. 8, 2004

(65) Prior Publication Data

US 2006/0079953 A1  Apr. 13, 2006

(51) Int. Cl.
*A61F 2/06* (2006.01)

(52) U.S. Cl. .................... 623/1.15; 623/901

(58) Field of Classification Search ...... 623/1.11–1.48, 623/901; 606/198, 194
See application file for complete search history.

(56) References Cited

U.S. PATENT DOCUMENTS

| | | | |
|---|---|---|---|
| 5,195,969 | A | 3/1993 | Wang et al. |
| 5,270,086 | A | 12/1993 | Hamlin |
| 5,366,504 | A | 11/1994 | Andersen et al. |
| 5,383,892 | A | 1/1995 | Cardon et al. |
| 5,674,242 | A | 10/1997 | Phan et al. |
| 5,780,807 | A | 7/1998 | Saunders |
| 5,980,553 | A | 11/1999 | Gray et al. |
| 6,017,362 | A * | 1/2000 | Lau ........................... 623/1.2 |
| 6,071,298 | A * | 6/2000 | Lashinski et al. ........... 606/198 |
| 6,106,642 | A | 8/2000 | DiCarlo et al. |
| 6,451,052 | B1 | 9/2002 | Burmeister et al. |
| 6,485,507 | B1 | 11/2002 | Walak et al. |
| 6,565,599 | B1 | 5/2003 | Hong et al. |
| 6,616,689 | B1 | 9/2003 | Ainsworth et al. |
| 6,629,994 | B2 | 10/2003 | Gomez et al. |
| 6,652,576 | B1 | 11/2003 | Stalker |
| 6,656,220 | B1 | 12/2003 | Gomez et al. |
| 6,726,712 | B1 | 4/2004 | Raeder-Devens et al. |
| 7,048,767 | B2 * | 5/2006 | Namavar ................ 623/23.6 |
| 2002/0144757 | A1 | 10/2002 | Craig et al. |
| 2003/0003220 | A1 | 1/2003 | Zhong et al. |
| 2003/0018380 | A1 | 1/2003 | Craig et al. |
| 2003/0077200 | A1 | 4/2003 | Craig et al. |
| 2003/0185895 | A1 | 10/2003 | Lanphere et al. |
| 2004/0088043 | A1 | 5/2004 | Klein |
| 2004/0143317 | A1 | 7/2004 | Stinson et al. |
| 2004/0186554 | A1 * | 9/2004 | Banas et al. ............. 623/1.15 |
| 2004/0191404 | A1 | 9/2004 | Hossainy et al. |
| 2005/0131522 | A1 * | 6/2005 | Stinson et al. ........... 623/1.15 |
| 2006/0259126 | A1 * | 11/2006 | Lenz ....................... 623/1.16 |
| 2007/0084530 | A1 * | 4/2007 | Boehlert ................... 148/670 |

OTHER PUBLICATIONS

Schetsky, L. McDonald, "Shape Memory Alloys", Encyclopedia of Chemical Technology (3rd ed.), John Wiley & Sons, 1982, vol. 20, pp. 726-736.

International Search Report received in PCT Application No. PCT/US2005/036420, mailed Feb. 16, 2006.

* cited by examiner

*Primary Examiner*—Suzette Gherbi
(74) *Attorney, Agent, or Firm*—Fish & Richardson P.C.

(57) ABSTRACT

Medical devices, such as endoprostheses, and methods of making the devices are disclosed. In some embodiments, an endoprosthesis includes a first portion having a first width, and a second portion having a second width different than the first width, wherein the first and second portions have different grain sizes.

31 Claims, 4 Drawing Sheets

MEDICAL DEVICES AND METHODS OF MAKING THE SAME

TECHNICAL FIELD

The invention relates to medical devices, such as stents, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

SUMMARY

The invention relates to medical devices, such as endoprostheses, and methods of making the medical devices.

In one aspect, the invention features a medical device, such as an endoprosthesis, having microstructures (e.g., grain sizes) that are tailored to particular dimensions of the device. The medical device can have enhanced mechanical performance. For example, the device can have good fatigue resistance, good strength, and/or low recoil.

In another aspect, the invention features an endoprosthesis, including a first portion having a first width, and a second portion having a second width different than the first width, wherein the first and second portions have different grain sizes.

Embodiments may include one or more of the following features. The endoprosthesis has a band including the first portion. The band has an ASTM E112 G value of about eight or more. The endoprosthesis includes an elongated portion extending from the band, the elongated portion having the second portion. The elongated portion has an ASTM E112 G value of about eight or less. The band is wider than the elongated portion. The band has a grain size larger than a grain size of the elongated portion. The band has a yield strength lower than a yield strength of the elongated portion. The first and second portions have different thicknesses. The first and second portions have different yield strengths. The first and second portions include a first material selected from the group of stainless steel, a radiopaque element, and an alloy including cobalt and chromium. The first portion is wider than the second portion, and the first portion has a grain size larger than a grain size of the second portion. The first portion has a yield strength lower than a yield strength of the second portion, and the first width is larger than the second width. The endoprosthesis includes a band including the first portion and the second portion.

In another aspect, the invention features an endoprosthesis, including a band having a first grain size, and an elongated portion extending from the band, the elongated portion having a second grain size different than the first grain size.

Embodiments may include one or more of the following features. The first grain size is larger than the second grain size. The band has a width larger than a width of the elongated portion. The band has an ASTM E112 G value of about eight or less. The elongated portion has an ASTM E112 G value of about eight or more. The band has yield strength lower than a yield strength of the elongated portion. The band and the elongated portion have the same thickness. The band and the elongated portion have different thicknesses. The band and the elongated portion have the same composition.

In another aspect, the invention features an endoprosthesis, including a first portion having a first width, and a second portion having a second width different than the first width, wherein the first and second portions have different yield strengths.

Embodiments may include one or more of the following features. The endoprosthesis includes a band including the first portion, and an elongated portion extending from the band and including the second portion, wherein the band has a yield strength lower than a yield strength of the elongated portion. The first width is larger than the second width. The first and second portions have different thicknesses. The first and second portions have the same composition. The endoprosthesis includes a band including the first portion and second portion.

In another aspect, the invention features a method of making an endoprosthesis, including forming a first portion of the endoprosthesis to have a first grain size, and forming a second portion of the endoprosthesis to have a second grain size different than the first grain size.

Embodiments may include one or more of the following features. The method further includes masking the endoprosthesis. The method further includes contacting the endoprosthesis with a laser beam. The method includes subjecting the first and second portions to different heat treatments. The endoprosthesis includes a band having the first portion, and an elongated portion extending from the band and having the second portion, the first grain size is larger than the second grain size, and the first portion has yield strength lower than a yield strength of the second portion.

In another aspect, the invention features a method of making an endoprosthesis, including forming a first portion of the endoprosthesis to have a first yield strength, and forming a second portion of the endoprosthesis to have a second yield strength different than the first yield strength.

Embodiments may include one or more of the following features. The method further includes masking the endoprosthesis. The method further includes contacting the endoprosthesis with a laser beam. The method includes subjecting the first and second portions to different heat treatments. The endoprosthesis includes a band having the first portion, and an elongated portion extending from the band and having the second portion, and the first yield strength is less than the second yield strength.

In another aspect, the invention features a medical device including one or more relatively coarse grain portions and one or more relatively fine grain portions. The medical device can be, for example, an orthopedic implant (such as a hip stem), a guidewire, or a hypotube.

Other aspects, features, and advantages will be apparent from the description of the preferred embodiments thereof and from the claims.

DETAILED DESCRIPTION

Figure 1:
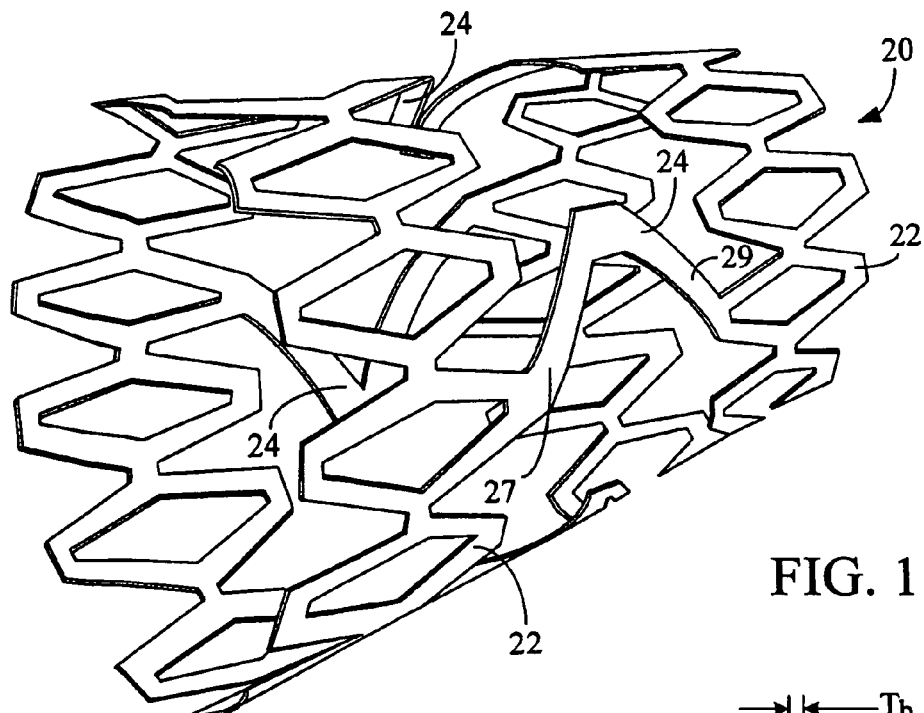
FIG. 1 is a perspective view of an embodiment of an expanded stent.

Referring to FIG. 1, a stent 20 has the form of a tubular member defined by a plurality of bands 22 and a plurality of connectors 24 that extend between and connect adjacent bands. During use, bands 22 are expanded from an initial, small diameter to a larger diameter to contact stent 20 against a wall of a vessel, thereby maintaining the patency of the vessel. Connectors 24 provide stent 20 with flexibility and conformability so that the stent can adapt to the contours of the vessel. Examples of stents are described in Burmeister et al., U.S. Pat. No. 6,451,052, and exemplified by the NIR® stent (Boston Scientific Corp.).

Figure 2:
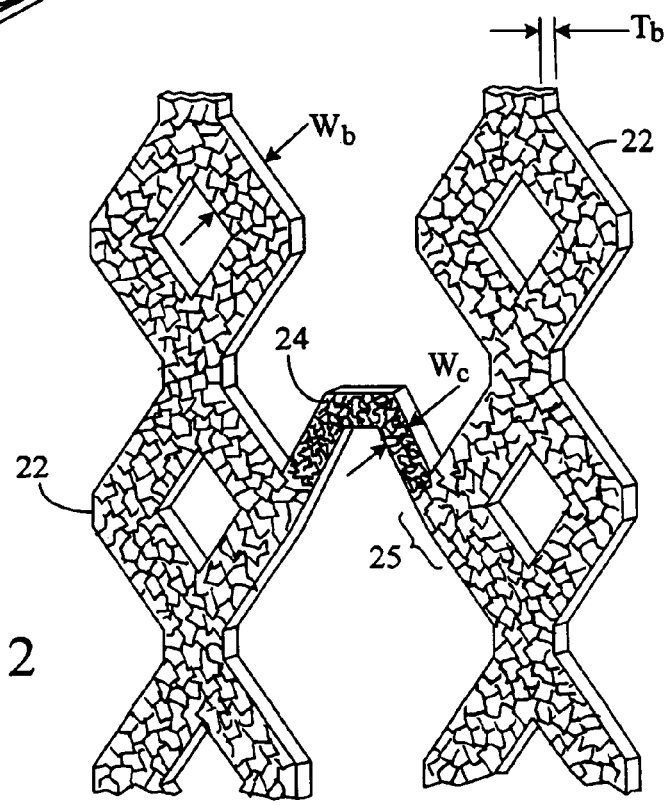
FIG. 2 is a detailed view of the stent of the FIG. 1.

Referring to FIG. 2, bands 22 and connectors 24 have different shapes and dimensions. As shown, the widths of the bands ($W_b$) are larger than the widths of the connectors ($W_c$). The larger widths ($W_b$) provide bands 22 with radial strength to support the vessel, and the smaller widths ($W_c$) allow connectors 24 to flex and to conform to the vessel. Connectors 24 are bent, having a first portion 27 that is not straight or collinear with a second portion 29. The bent shape of connectors 24 allows them to accommodate strain during expansion of stent 20. In other embodiments, connectors 24 include one or more curved portions, examples of which are described in U.S. Pat. Nos. 6,656,220; 6,629,994; and 6,616,689. As shown, bands 22 include a plurality of connected polygons, but other embodiments, such as sinusoidal waves or zigzag waves, can be used.

In addition, bands 22 and connectors 24 also have different microstructures. As shown, bands 22 and connectors 24 have different grain sizes, with the grains in the bands being larger than the grains in the connectors. As a result, connectors 24 have a higher yield strength that the yield strength of bands 22, since grain size is typically inversely related to yield strength. The high yield strength of connectors 24 allows them to have small cross-sectional sizes, which allows them to easily deform so that stent 20 can conform well to a vessel that is not straight. The yield strength and the section size are balanced to allow connectors 24 to easily deform while remaining resistant to fracture. In comparison, the low yield strength of bands 22 reduces elastic recoil when stent 20 is crimped to a delivery system and during in vivo expansion. The yield strength and the section size of bands 22 are balanced to provide good resistance to radial compression and to control elastic recoil.

Without wishing to be bound by theory, it is believed that stent 20 can experience relatively high levels of stress during use. For example, stent 20 can be bent as it tracks through a tortuous vessel during delivery, as it is expanded, and/or when it is placed in a curved vessel. After implantation, stent 20 can also experience stress from movement cause by a beating heart or by the subject's breathing. The stress can strain the relatively narrow connectors 24 and fracture the connectors. A fractured connector can provide surfaces that disrupt blood flow and/or provide sites on which blood can aggregate and undesirably lead to blood clotting or thrombosis in the vessel. By forming stent 20 with enhanced microstructures, and therefore enhanced mechanical properties, connectors 24 can tolerate the stress that can lead to fracture, while still being easily deformable. At the same time, bands 22 are able to have good radial strength to support the vessel.

As used herein, a band 22 refers to a portion of a stent that extends circumferentially about the stent. The band can extend completely about the circumference of a stent, for example, such that the ends of the band are joined, or the band can extend partially about the circumference. The band can extend substantially linearly or nonlinearly, for example, in an undulating pattern or a zigzag pattern as shown in FIG. 1. In some embodiments, bands 22 are connected together by integrally formed connectors that extend between and transversely to the bands. Band 22 can have a width ($W_b$) ranging from about 0.0010 inch to about 0.0075 inch. Particular widths of band 22 can be a function of, for example, the material(s) in stent 20, the type of stent (e.g., balloon-expandable or self-expandable), and/or the desired performance. For example, a stent including 316L stainless steel can have a band width ($W_b$) of from about 0.0025 inch to about 0.0075 inch; a stent including an alloy of 10-60 weight percent and 316L stainless steel constituents (PERSS®) can have a band width ($W_b$) of from about 0.0015 inch to about 0.0070 inch; and a stent including a Fe—Co—Cr—Ni alloy (such as Elgiloy, MP35N or L605) can have a band width ($W_b$) of from about 0.0010 inch to about 0.0065 inch; and a stent including niobium alloyed with about 1-10 weight percent zirconium, about 1-70 weight percent tantalum, or about 1-10 weight percent tungsten can have a band width ($W_b$) of from about 0.0030 inch to about 0.0075 inch.

In some embodiments, band 22 has at least nine grains per unit area. For example, per unit area, band 22 can have at least twelve grains, at least sixteen grains, at least 20 grains, at least 25 grains, at least 36 grains, or higher. As used herein, a unit area is the product of the width ($W_b$) and thickness ($T_b$) of band 22. The number of grains is an average number of grains taken over a substantial number (e.g., 20 or more) of cross sections of band 22.

Alternatively or additionally, the grain structure of band 22 can be expressed in terms of an average grain size (e.g., diameter). Table 1 shows how the average grain size (diameter) for four band widths ($W_b$) (0.10-0.25 mm) can be related to the number of grains per unit area.

TABLE 1

| Band Width ($W_b$) and Thickness ($T_b$) (mm) | Unit Area ($W_b \times T_b$) (mm$^2$) | Grain/Unit Area (9/T$^2$, grain/mm$^2$) | ASTM E112 G | Avg. Grain Diameter (microns) |
| --- | --- | --- | --- | --- |
| 0.254, 0.127 | 0.032258 | 279 | 5 | 64 |
| 0.204, 0.102 | 0.020808 | 433 | 6 | 45 |
| 0.152, 0.076 | 0.011552 | 779 | 7 | 32 |
| 0.102, 0.051 | 0.005202 | 1730 | 8 | 20 |

As indicated above, the unit area is determined by multiplying the width by the thickness of a band. The number of grains per unit area (in this example, nine grains/unit area) can then be converted to an ASTM E112 G value. (See ASTM E112 Table 4. Grain Size Relationships Computed for Uniform, Randomly Oriented, Equiaxed Grains.) The average grain diameter can then be determined from ASTM E112 G value, which is inversely proportional to the average grain diameter. (See ASTM E112.) In some embodiments, band 22 has an average ASTM E112 G value of about eight or less. The average grain diameter can range from about 20 microns to about 64 microns. For example, the average grain diameter can be equal to or less than about 64, about 60, about 56, about 52, about 48, about 44, about 40, about 36, about 32, about 28, or about 24 microns; and/or greater than or equal to about 20, about 24, about 28, about 32, about 36, about 40, about 44, about 48, about 52, about 56, or about 60 microns. In embodiments in which bands 22 include one or more refractory metals, such as niobium, tantalum, or tungsten, the grain size can be fine to reduce brittleness. The grain size can be, for example, less than about 32 microns, e.g., less than about 28 or 24 microns.

The microstructure (e.g., grain size) of bands 22 in turn can affect the mechanical properties of the bands. In some embodiments, bands 22 have yield strengths of from about 15 ksi to about 70 ksi. The relatively low yield strength (e.g., compared to the yield strength of connectors 24 described below) allows bands 22 to be plastically deformed during crimping of stent and during expansion of the stent with low recoil. The yield strength can be greater than or equal to about 15, about 20, about 25, about 30, about 35, about 40, about 45, about 50, about 55, about 60, or about 65 ksi; and/or less than or equal to about 70, about 65, about 60, about 55, about 50, about 45, about 40, about 35, about 30, about 25, or about 20 ksi. In certain embodiments, bands 22 including an alloy including cobalt can have a yield strength from about 40-60 ksi, bands including a refractory metal (such as niobium or tantalum) can have a yield strength from about 15-30 ksi, and bands including titanium metal can have a yield strength from about 25-40 ksi.

Similar to bands 22, connectors 24 are also tailored to provide predetermined properties and performance. As used herein, a connector 24 refers to a portion of a stent that extends from a band of the stent, for example, from a first band to an adjacent second band along the length of the stent. The connector can include one strut or a plurality of struts. The connector can extend linearly (e.g., parallel to the longitudinal axis of the stent) or nonlinearly, for example, in an undulating patter or zigzag pattern. Connector 24 can have a width ($W_c$) ranging from about 0.030 mm to about 0.200 mm. Particular widths of connector 24 can be a function of, for example, the material(s) in stent 20, the type of stent (e.g., balloon-expandable or self-expandable), and/or the desired performance. For example, a stent including 316L stainless steel can have a connector width ($W_c$) of from about 0.05 mm to about 0.12 mm; a stent including a PERSS® alloy can have a band width ($W_c$) of from about 0.03 mm to about 0.10 mm; a stent including an alloy having chromium and cobalt can have a band width ($W_c$) of from about 0.02 mm to about 0.08 mm; a stent including a refractory metal can have a band width ($W_c$) of from about 0.08 mm to about 0.20 mm; and a stent including an alloy having titanium can have a band width ($W_c$) of from about 0.03 mm to about 0.15 mm.

As with band 22, in some embodiments, connector 24 has at least nine grains per unit area. For example, per unit area, connector 24 can have at least twelve grains, at least sixteen grains, at least 20 grains, at least 25 grains, at least 36 grains, or higher. Here, a unit area is the product of the width ($W_c$) and thickness ($T_c$) of connector 24 (FIG. 4). The number of grains is an average number of grains taken over a substantial number (e.g., 20 or more) of cross sections of connector 24.

Alternatively or additionally, the grain structure of connector 24 can be expressed in terms of an average grain size (e.g., diameter), which can be determined as described above but using $W_c$. Since connector 24 is narrower (and/or thinner) than band 22 in some embodiments, the grain size of the connector is smaller than the grain size of the band, e.g., to provide at least nine grains per unit area. In some embodiments, connector 24 has an average ASTM E112 G value of about eight or more, including nanometer size grains that are off of the ASTM E112 G scale. The average grain diameter can range from about 30 microns to about 0.01 microns (10 nanometers). For example, the average grain diameter can be equal to or less than about 30, about 25, about 20, about 15, about 10, about 5, about 1, about 0.50, about 0.25, about 0.10, or about 0.05 micron; and/or greater than or equal to about 0.01, about 0.05, about 0.10, about 0.25, about 0.50, about 1, about 5, about 10, 1 about 5, about 20, or about 25 microns. In certain embodiments, the grain size can be from about 0.1 to about 20 microns for connectors 24 including a stainless steel, from about 1 to about 30 microns for connectors including an alloy having cobalt, from about 10 to about 20 microns for connectors including a refractory metal, and from about 0.1 to about 20 microns for connectors including an alloy having titanium.

The microstructure (e.g., grain size) of connectors 24 in turn can affect the mechanical properties of the connectors. For example, a fine grain size can result in a high yield strength, which in turn allows the connector to be made thin and flexible. In some embodiments, connectors 24 have yield strengths of from about 35 ksi to about 100 ksi. The relatively high yield strength (e.g., compared to the yield strength of bands 22 described above) allows connectors 24 to resist fatigue failure during delivery of stent 20 and after stent placement. The yield strength can be greater than or equal to about 35, about 40, about 45, about 50, about 55, about 60, about 65, about 70, about 75, about 80, about 85, about 90, or about 95 ksi; and/or less than or equal to about 100, about 95, about 90, about 85, about 80, about 75, about 70, about 65, about 60, about 55, about 50, about 45, or about 40 ksi. In some embodiments, the yield strength can be from about 45 to about 90 ksi for connectors including stainless steel, from about 50 to about 100 ksi for connectors including an alloy having cobalt, from about 35 to about 60 ksi for connectors including a refractory metal, and from about 40 to about 80 ksi for connectors including an alloy having titanium.

Intermediate portions between bands 22 and connectors 24 (e.g., portion 25, FIG. 2) can have microstructures intermediate that of the bands and the connectors. In some embodiments, the intermediate portions include a gradient of microstructures that includes coarse grains (e.g., near the bands) transitioning to fine grains (e.g., near the connectors). The gradient reduces an abrupt change that can be susceptible to stress and fracture. The intermediate portions can be formed, for example, by tapering a thermal barrier or mask, as described below. In some embodiments, the intermediate portions can extend over lengths of from about 10 to 200 microns or about 5 to 20 times the average grain diameter of connector 24. For example, the intermediate portion between a band with 32 micron grains to a connector with 10 micron grains can extend over a length of 50 microns. One or more intermediate portions can be located away from the intersection of a connector 24 and a band 22, such as within the band, to reduce stress concentrations in the small connector and at the change in width from the connector to band.

Bands 22 and connectors 24 can include (e.g., be manufactured from) one or more biocompatible materials with mechanical properties so that stent 20 can be compacted, and subsequently expanded to support a vessel. In some embodiments, stent 20 can have an ultimate tensile strength (UTS) of about 20-150 ksi, greater than about 15% elongation to failure, and a modulus of elasticity of about 10-60 msi. When stent 20 is expanded, the material can be stretched to strains on the order of about 0.3. Examples of "structural" materials that provide good mechanical properties and/or biocompatibility include, for example, stainless steel (e.g., 316L and 304L stainless steel, and PERSS®), Nitinol (a nickel-titanium alloy), Elgiloy, L605 alloys, MP35N, Ti-6Al-4V, Ti-50Ta, Ti-10Ir, Nb-1Zr, and Co-28Cr-6Mo. Other materials include elastic biocompatible metal such as a superelastic or pseudo-elastic metal alloy, as described, for example, in Schetsky, L. McDonald, "Shape Memory Alloys", Encyclopedia of Chemical Technology (3rd ed.), John Wiley.& Sons, 1982, vol. 20. pp. 726-736; and commonly assigned U.S. Ser. No. 10/346,487, filed Jan. 17, 2003.

The material(s) can include one or more radiopaque materials to provide radiopacity. Examples of radiopaque materials include metallic elements having atomic numbers greater than 26, e.g., greater than 43. In some embodiments, the radiopaque materials have a density greater than about 9.9 g/cc. In certain embodiments, the radiopaque material is relatively absorptive of X-rays, e.g., having a linear attenuation coefficient of at least 25 $cm^{-1}$, e.g., at least 50 $cm^{-1}$, at 100 keV. Some radiopaque materials include tantalum, platinum, iridium, palladium, hafnium, tungsten, gold, ruthenium, and rhenium. The radiopaque material can include an alloy, such as a binary, a ternary or more complex alloy, containing one or more elements listed above with one or more other elements such as iron, nickel, cobalt, or titanium. Examples of alloys including one or more radiopaque materials are described in U.S. Application Publication US-2003-0018380-A1; US-2002-0144757-A1; and US-2003-0077200-A1.

In some embodiments, stent 20 includes one or more materials that enhance visibility by magnetic resonance imaging (MRI). Examples of MRI materials include non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni). Alternatively or in addition, stent 20 can include one or more materials having low magnetic susceptibility to reduce magnetic susceptibility artifacts, which during imaging can interfere with imaging of tissue, e.g., adjacent to and/or surrounding the stent. Low magnetic susceptibility materials include tantalum, platinum, titanium, niobium, copper, and alloys containing these elements. The MRI visible materials can be incorporated into the structural material, can serve as the structural material, and/or be includes as a layer of stent 20.

Stent 20 can be of any desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. Stent 20 can be balloon-expandable, self-expandable, or a combination of both (e.g., U.S. Pat. No. 5,366,504).

Figure 3:
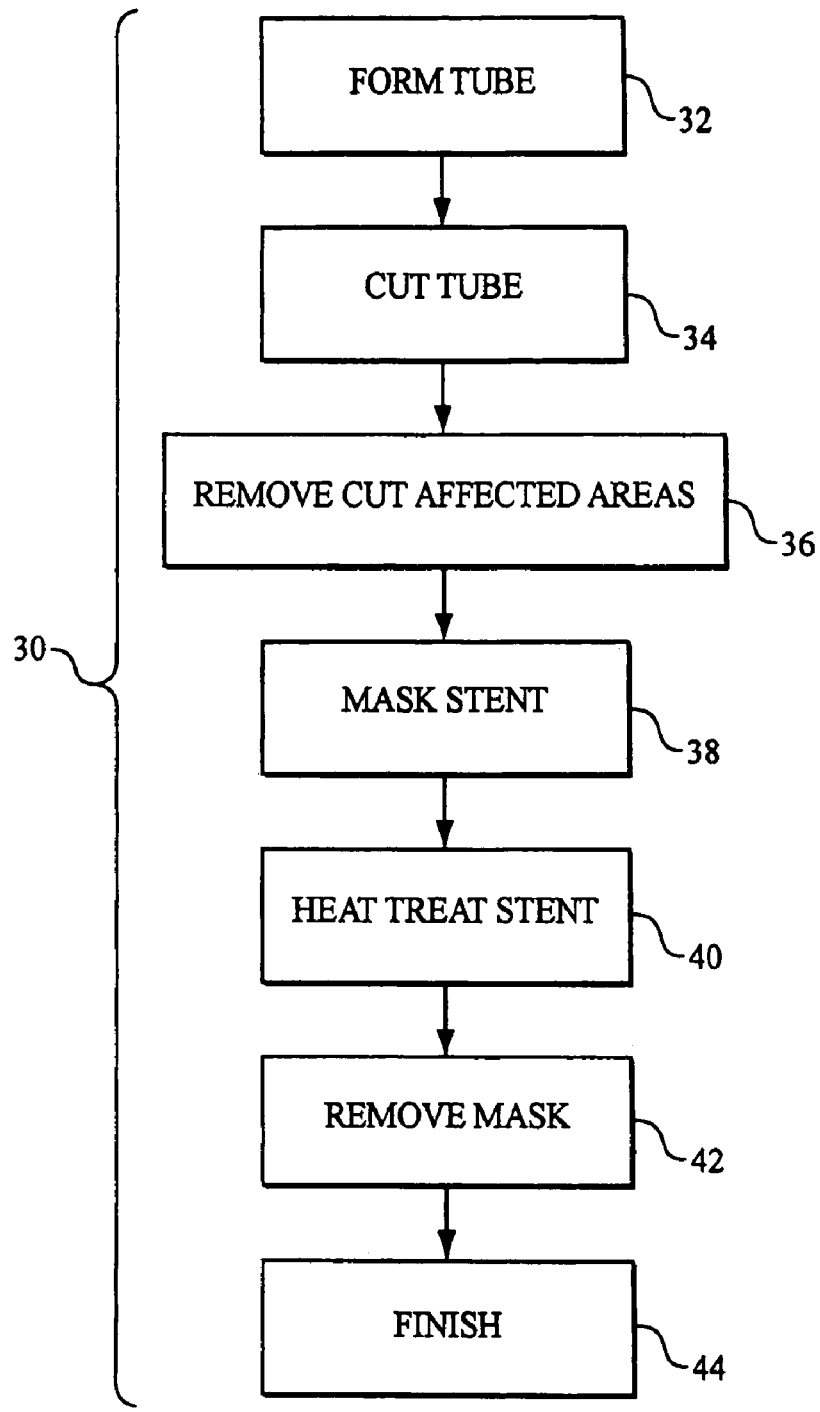
FIG. 3 is a flow chart of an embodiment of a method of making a stent.

Stent 20 can be formed by heat treating bands 22 and connectors 24 differently. FIG. 3 shows a method 30 of making stent 20. As shown, method 30 includes forming a tube (step 32) that makes up the tubular member of stent 20. The tube is subsequently cut to form bands 22 and connectors 24 (step 34) to produce an unfinished stent. Areas of the unfinished stent affected by the cutting are subsequently removed (step 36). Next, selected portions of bands 22 and/or connectors 24 are masked in a predetermined manner to allow the bands and the connectors to be heat treated differently (step 38). The masked unfinished stent is then heat treated, e.g., using a laser (step 40). Next, the mask is removed (step 42), and the unfinished stent is finished to form stent 20 (step 44).

The tube that makes up the tubular member of stent 20 can be formed using metallurgical techniques, such as thermo-mechanical processes (step 32). For example, a hollow metallic member (e.g., a rod or a bar) can be drawn through a series of dies with progressively smaller circular openings to plastically deform the member to a targeted size and shape. In some embodiments, the plastic deformation strain hardens the member (and increases its yield strength) and elongates the grains along the longitudinal axis of the member. The deformed member can be heat treated (e.g., annealed above the recrystallization temperature and/or hot isostatically pressed) to transform the elongated grain structure into an initial grain structure, e.g., one including equi-axed grains. Small or fine grains can be formed by heating the member close to the recrystallization temperature for a short time. Large or coarse grains can be formed by heating the member at higher temperatures and/or for longer times to promote grain growth.

Next, bands 22 and connectors 24 of stent 20 are formed, as shown, by cutting the tube (step 34). Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, is flowed through the lumen of the tube.

The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above can be removed (step 36). For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing). In some embodiments, the tubular member can be near net shape configuration after step 36 is performed. "Near-net size" means that the tube has a relatively thin envelope of material that is removed to provide a finished stent. In some embodiments, the tube is formed less than about 25% oversized, e.g., less than about 15%, 10%, or 5% oversized.

Figure 4A:
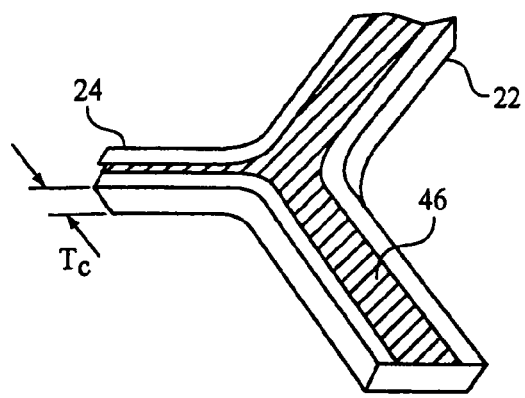
FIGS. 4A, 4B, and 4C illustrate an embodiment of a method of masking a tube.
Figure 4B:
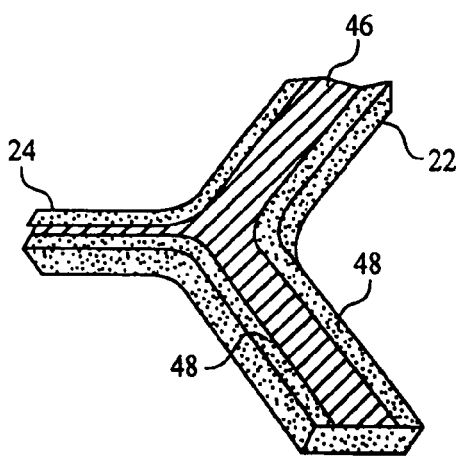
Figure 4C:
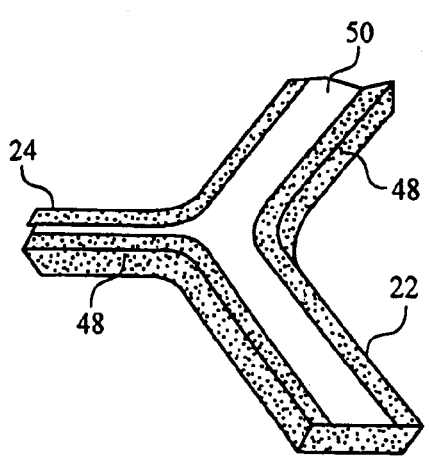

Next, selected portions of bands 22 and connectors 24 are masked (step 38). Referring to FIGS. 4A, 4B, and 4C, an embodiment of a method for masking bands 22 and connectors 24 is shown. A removable shield 46 is first placed on bands 22 and connectors 24 over portions that are to be exposed during heat treatment (FIG. 4A). Shield 46 can be, for example, an adhesive-backed tape; a dissolvable material (such as a carbon steel that can be dissolved by immersion in an acid such as nitric acid, which can also remove certain recast material formed during manufacturing); or a material (such as gallium metal) that can be melted or sublimed during heat treatment. Shield 46 can include a ceramic and/or a glass that can be removed by heating the tube and allowing differential thermal expansion to separate the shield from the tube. Alternatively or in addition, shield 46 can be removed mechanically, such as by grinding.

Next, a mask 48 is applied over bands 22 and connectors 24 to serve as an insulative thermal barrier (FIG. 4B). Examples of materials for mask 48 include ceramics (such as titanium nitride, titanium carbide, and silicon carbide), including oxides (such as aluminum oxide, zirconium oxide, and magnesium oxide). Mask 48 can be applied by slurry dipping, spraying, powder coating, physical vapor deposition, sputtering, and/or chemical vapor deposition. Shield 46 is then removed to expose the previously shielded portions 50 of bands 22 and connectors 24 (FIG. 4C). Masking bands 22 and connectors 24 allow the bands and the connectors to be heat treated differently, as described below. Masking also allows selected small areas of the unfinished stent to be locally and thoroughly heated without substantial heat loss because the open structure of the unfinished stent can radiate heat.

Referring again to FIG. 3, after the unfinished stent is masked, the unfinished stent is heat treated (step 40). For example, the unfinished stent can be heated, under vacuum or under a controlled (e.g., inert) atmosphere, in a furnace, in an induction coil, or under a heat lamp. As shown in FIG. 4C, connector 24 is more masked than band 22. As a result, when connector 24 and band 22 are heated under the same conditions, the band experiences more heating and grain growth. In some embodiments, alternatively or additionally to covering different percentages of surface areas of bands 22 and connectors 24, different thicknesses of mask 48 can be deposited to effect different heating. For example, mask 48 on connectors 24 can be thicker than the mask on bands 22 to provide more insulation and therefore less heating.

Alternatively or additionally to heating as above, exposed portions 50 can be locally heated so that the heat treated areas are precisely targeted. For example, exposed portions 50 can be addressed with a laser, an electron beam, or other focal heating sources, such that the heat is conducted from exposed portions 50 to the bulk of the tube. In some embodiments of local heating, connectors 24 can be less masked than bands 22 to dissipate heat.

In some embodiments, bands 22 and connectors 24 are not masked prior to heat treatment. Bands 22 and connectors 24 can be heat treated differently, for example, by lasing the bands for longer times and/or with more energy to produce grain growth, compared to lasing the connectors. In embodiments in which the initial grain structure of the tube is the desired grain structure of connectors 24, only the connectors can be masked (e.g., if not using local heating) and/or only bands 22 are heat treated to effect grain growth.

After the unfinished stent is heat treated to form the targeted microstructures, mask 48 is removed (step 42). Mask 48 can be removed by, for example, grit blasting, chemical milling, and/or cryogenic fracture.

The unfinished stent is then finished to form stent 20. The unfinished stent can be finished, for example, by electropolishing to a smooth finish. Since the unfinished stent can be formed to near-net size, relatively little of the unfinished stent need to be removed to finish the stent. As a result, further processing (which can damage the stent) and costly materials can be reduced. In some embodiments, about 0.0001 inch of the stent material can be removed by chemical milling and/or electropolishing to yield a stent.

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

In some embodiments, bands 22 and connectors 24 can have the same thickness or different thicknesses. A smaller thickness, for example, can enhance the flexibility of connectors 24.

Alternatively or additionally to masking bands 22 and connectors 24, the unfinished stent can be selectively coated with a polished and reflective coating (e.g., on the connectors) and/or a blackened coating (e.g., on the bands). The polished and reflective coating (such as gold, platinum, and/or silver) can reduce the amount of heat transferred to the unfinished stent. The blackened coating (such as graphite) can increase the amount of heat transferred to the unfinished stent.

In some embodiments, no masking is necessary. For example, a tube as described herein can be fixtured into a laser-cutting machine. The tube can be heat treated using a de-focused laser and computer-numeric control. For example, the laser can be controlled to heat the areas of the tube that will eventually be cut to form bands 22 at a temperature below the melting point of the tube material. Heat dispersion can be accomplished by flowing a coolant through the lumen of the tube. After the heat treatment, the laser can be re-focused to cut bands 22 and connectors 24, without removing the tube from the fixture. Connectors 24 can have a higher yield strength and a smaller grain size than bands 22 because the bands have been heat treated.

In some embodiments, bands 22 and/or connectors 24 can include multiple widths and/or thicknesses. For example, a band can include a first large width and a second smaller width. The first large width can have a microstructure as described above for band 22, and the second smaller width can have a microstructure as described above for connector 24. A connector having multiple widths and/or thicknesses can include similar microstructures.

Stent 20 can include one or more layers. For example, a stent can include a first "structural" layer, such as 316L stainless steel, and a second layer of a radiopaque element. The radiopaque layer can be formed after the heat treatment to prevent, e.g., separation due to thermal expansion differences. Either layer can be the inner or the outer layer, and either layer or both layers can include the microstructures as described above. A three-layered stent can include a layer including a radiopaque element formed between two structural layers.

Stent 20 can also be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

Figure 5:
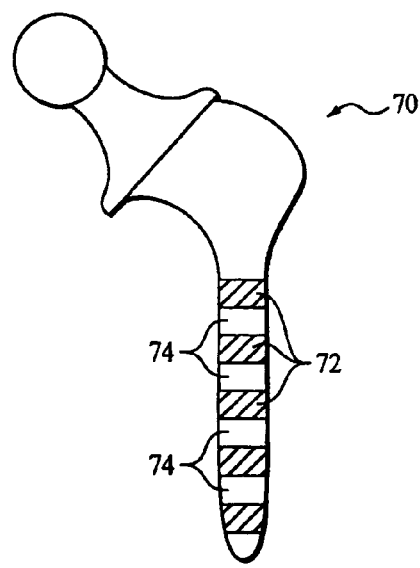
FIG. 5 is a lateral view of an embodiment of a hip stem.

In other embodiments, the structures and methods described herein can be used to make other medical devices. For example, referring to FIG. 5, an orthopedic device (as shown, a hip stem 70) can be formed to include one or more stiff or rigid sections 72, and one or more flexible sections 74 along the length of the device (e.g., stem) to provide the device with an overall stiffness similar to that of natural bone. As shown, stem 70 has a long, tapered cylindrical shape, and along its length, the stem includes relatively large diameter rigid sections 72 alternating with adjacent, relatively small diameter flexible sections 74. Rigid sections 72 can be made with a selected grain size that provides a targeted yield strength, and small diameter sections 74 can be made with finer grain size to provide a higher yield strength. Stem 70 can flex in flexible sections 74, but not yield or fracture in these sections because the higher local yield strength can prevent plastic deformation. In some embodiments, to reduce abrupt changes between sections 72 and 74 that can concentrate stress, one section can be tapered to the adjacent section, and within the taper, the grain size can transition, similar to the intermediate portions described above. Stem 70 can be made flexible, strong, and fracture resistant. In some embodiments, sections 72 and 74 can have varying dimensions along the length of stem 70 so that the sections alternate with different frequencies along the length.

Figure 6A:
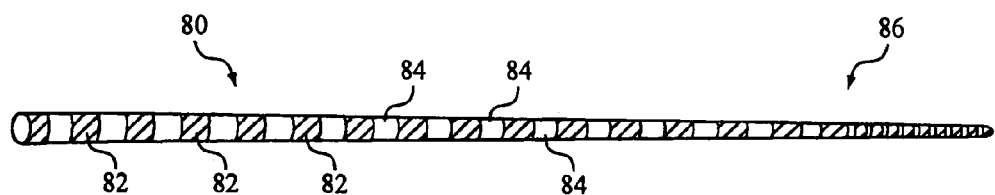
FIGS. 6A and 6B are lateral views of embodiments of guide wires.
Figure 6B:
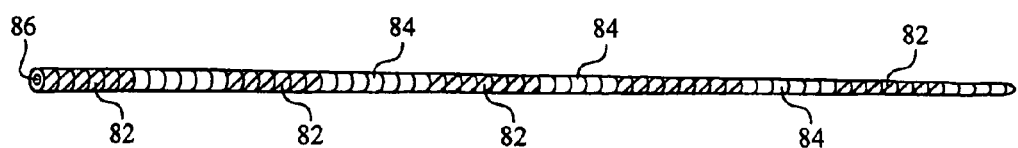

As another example, guidewires can be made of strong materials that have good radiopacity and torquability (such as cobalt alloys and stainless steels) and be controllably processed to provide good flexibility for enhanced trackability. For example, referring to FIG. 6A, a guidewire 80 includes a plurality of coarse grain sections (e.g., bands) 82 alternating with a plurality of fine grain sections 84 along the tapered length of the guidewire. Coarse grain sections 82, which can be larger (e.g., in diameter) than sections 84, can provide guidewire 80 with a targeted stiffness. Fine grain sections 84 can allow guidewire 80 to flex to enhance trackability, while not yielding or fracturing because the relatively high local yield strength can prevent plastic deformation. Similar to hip stem 70 above, the dimensions, distribution and frequency of sections 82 and 84 can vary along the length of guidewire 80, for example, to make the distal tip 86 of the guidewire particularly flexible. Guidewire 80 can be solid (as shown in FIG. 6A) or hollow. For example, referring to FIG. 6B, a ribbon having sections 82 and 84 can be tightly wound to form a guidewire defining a lumen 86.

The following examples are illustrative and not intended to be limiting.

EXAMPLE 1

The following example illustrates a method of making a stent including a stainless steel, such as 316L stainless steel.

A 316L stainless steel hollow bar can be gundrilled and machined (1.0" O.D.×0.08" I.D., from a 1.1" diameter bar) and can be drawn to form a stent tubing with an O.D. of 0.10" and an I.D. of 0.08". The final cold working operation, following the last recrystallization anneal treatment, can be performed to produce 40-60% cold work in the material. The resulting tube can have textured (elongated) grains.

The tubing can be laser machined to cut a pattern of bands with a width of 0.13 mm and thickness of 0.06 mm, and a pattern of connectors with a width of 0.06 mm and thickness of 0.06 mm to form an unfinished stent. Laser affected areas can be removed by chemical etching and electropolishing.

A maskant system can be applied to the unfinished stent such that the bands can receive more heat than the connectors during an annealing treatment. The maskant can be porous layers of iron deposited by a laser or a plasma spray. The pore size of the maskant can be larger for the band surfaces (e.g., 70% porosity) than the connector surfaces (e.g., 20% porosity). The total thickness of the maskant can be about 0.06-0.10 mm on all surfaces. The unfinished stent can then be bright annealed by passing it through a furnace with a protective hydrogen atmosphere on a conveyor belt such that the unfinished stent can be exposed to a temperature of 1050° C. for 10 minutes. Afterwards, the unfinished stent can be cooled in protective atmosphere, and the maskant can be dissolved away in a nitric acid solution.

The unfinished stent can then be finished by electropolishing to a final size and surface finish. The finished stent can have coarser grains in the bands than in the connectors. The average grain size of the bands can be about 45 microns, and the average grain size of the connectors can be about 11 microns. The yield strengths can be about 40 ksi for the bands, and about 55 ksi for the connectors.

EXAMPLE 2

The following example illustrates a method of making a stent including an alloy of stainless steel and platinum.

A PERSS® stainless steel (Fe-30 Pt-18 Cr-9 Ni-2.63 Mo) hollow bar can be gundrilled and machined (1.0" O.D.× 0.08" I.D., from 1.1" diameter bar) and can be drawn to form a stent tubing with an O.D. of 0.10" and an I.D. of 0.08". The final cold working operation, following the last recrystallization anneal treatment, can be performed to produce 40-60% cold work in the material. The resulting tube can include textured (elongated) grains.

The tubing can be laser machined to cut a pattern of bands with a width of 0.13 mm and a thickness of 0.03 mm, and a pattern of connectors with a width of 0.06 mm and thickness of 0.03 mm to form an unfinished stent. Laser affected areas can be removed by chemical etching and electropolishing.

A laser deposited maskant system can be applied to the connectors such that the bands can receive more heat than the connectors during an annealing treatment. The maskant deposited on the surface of the connectors can be a continuous layer of iron that triples the thickness of the wall of the unfinished stent wall. The added thickness can slow the heating rate of the connectors, thereby reducing the time of exposure at the anneal temperature. The unfinished stent can then be bright annealed by passing it through a furnace with a protective hydrogen atmosphere on a conveyor belt such that the unfinished stent can be exposed to a temperature of 1165° C. for 10 minutes. Afterwards, the unfinished stent can be cooled in a protective atmosphere, and the maskant can be dissolved away in a nitric acid solution.

The unfinished stent can then be finished by electropolishing to a final size and surface finish. The finished stent can have coarser grains in the bands than in the connectors. The average grain size of the bands can be about 53 microns, and the average grain size of the connectors can be about 11 microns. The yield strengths can be about 55 ksi for the bands and about 80 ksi for the connectors.

EXAMPLE 3

The following example illustrates a method of making a stent including a Co—Cr alloy.

An L605 alloy (51Co-20Cr-10Ni-15W-3Fe-2Mn) hollow bar can be gundrilled and machined (1.0" O.D.x0.08" I.D., from 1.1" diameter bar) and can be drawn to form a stent tubing with an O.D. of 0.10" and an I.D. of 0.08". The final cold working operation, following the last recrystallization anneal treatment, can be performed to produce 40-60% cold work in the material. The resulting tube can have textured (elongated) grains.

The tubing can be laser machined to cut a pattern of bands with a width of 0.13 mm and thickness of 0.03 mm, and a pattern of connectors with a width of 0.06 mm and thickness of 0.03 mm to form an unfinished stent. Laser affected areas can be removed by chemical etching and electropolishing.

A maskant system can be applied to the unfinished stent such that the bands can receive more heat than the connectors during an annealing treatment. The unfinished stent can be dipped in a ceramic solution containing zirconia or alumina and allowed to dry. The coating on the bands can later be grit blasted away. Only the exterior surface of the unfinished stent need be grit blasted, since this exposed metal can allow sufficient heat input to cause recrystallization and grain growth. The unfinished stent can then be bright annealed by passing it through a furnace with a protective hydrogen atmosphere on a conveyor belt such that the unfinished stent can be exposed to a temperature of 1250° C. for 10 minutes. Afterwards, the unfinished stent can be cooled in a protective atmosphere, and the maskant can be removed by liquid media honing.

The unfinished stent can be finished by electropolishing to a final size and surface finish. The finished stent can have coarser grains in the bands than in the connectors. The average grain size of the bands can be about 53 microns, and the average grain size for the connectors can be about 11 microns. The yield strengths can be about 55 ksi for the bands, and about 80 ksi for the connectors.

EXAMPLE 4

The following example illustrates a method of making a stent including an alloy containing niobium and zirconium.

A Nb-1Zr hollow bar can be gundrilled and machined (1.0" O.D.x0.08" I.D., from 1.1" diameter bar) and can be drawn to form a stent tubing with an O.D. of 0.10" and an I.D. of 0.08". The final cold working operation, following the last recrystallization anneal treatment, can be performed to produce 40-60% cold work in the material. The resulting tube can have textured (elongated) grains.

The tubing can be laser machined to cut a pattern of bands with a width of 0.13 mm and thickness of 0.10 mm, and a pattern of connectors with a width of 0.10 mm and thickness of 0.10 mm to form an unfinished stent. Laser affected areas can be removed by chemical etching and electropolishing.

A maskant system can be applied to the unfinished stent such that the bands can receive more heat than the connectors during an annealing treatment. The maskant can be a vapor deposited, highly reflective gold layer. The exterior surfaces of the bands can first be covered with strips of adhesive tape. The unfinished stent can then be vapor deposited with gold. The strips of tapes can be peeled off the bands such that the gold on the strips are removed from the unfinished stent. The unfinished stent can then be vacuum annealed by loading it into a vacuum heat treat furnace chamber and programming the furnace such that the unfinished stent can be exposed to a temperature of 1300° C. for 30 minutes. The reflective surfaces on the connectors can reduce the heating rate of the connectors such that the connectors have less time at 1300° C. than the bands. Afterwards, the unfinished stent can be cooled in a protective atmosphere, and the maskant can be dissolved away.

The unfinished stent can be finished by electropolishing to a final size and surface finish. The finished stent can have coarser grains in the bands than in the connectors. The average grain size of the bands can be about 23 microns, and the average grain size for the connectors can be about 8 microns. The yield strengths can be about 30 ksi for the bands, and about 50 ksi for the connectors.

All publications, references, applications, and patents referred to herein are incorporated by reference in their entirety.

Other embodiments are within the claims.

What is claimed is:

1. An endoprosthesis, comprising
a band including a first portion and a second portion:
the first portion having a first width, the first portion having an ASTM E112 G value of about eight or more; and
the second portion having a second width different than the first, wherein the first and second portions have different grain sizes; and
an elongated portion extending from the band.

2. The endoprosthesis of claim 1, wherein the elongated portion is bent.

3. The endoprosthesis of claim 1, wherein the second portion has an ASTM E112 G value of about eight or less.

4. The endoprosthesis of claim 1, wherein the band is wider than the elongated portion.

5. The endoprosthesis of claim 1, wherein the first portion has a grain size larger than a grain size of the second portion.

6. The endoprosthesis of claim 1, wherein the first portion has a yield strength lower than a yield strength of the second portion.

7. The endoprosthesis of claim 1, wherein the first and second portions have different thicknesses.

8. The endoprosthesis of claim 1, wherein the first and second portions have different yield strengths.

9. The endoprosthesis of claim 1, wherein the first and second portions comprise a first material selected from the group of stainless steel, a radiopaque element, and an alloy including cobalt and chromium.

10. The endoprosthesis of claim 1, wherein the first portion is wider than the second portion, and the first portion has a grain size larger than a grain size of the second portion.

11. The endoprosthesis of claim 1, wherein the first portion has a yield strength lower than a yield strength of the second portion, and the first width is larger than the second width.

12. An endoprosthesis, comprising:
   a band having a first grain size and a band median width; and
   an elongated portion extending from the band, the elongated portion having a second grain size smaller than the first grain size and an elongated portion median width different than the band median width.

13. The endoprosthesis of claim 12, wherein the band median width is larger than the elongated portion median width.

14. The endoprosthesis of claim 12, wherein the band has an ASTM E112 G value of about eight or less.

15. The endoprosthesis of claim 12, wherein the elongated portion has an ASTM E112 G value of about eight or more.

16. The endoprosthesis of claim 12, wherein the band has yield strength lower than a yield strength of the elongated portion.

17. The endoprosthesis of claim 12, wherein the band and the elongated portion have the same thickness.

18. The endoprosthesis of claim 12, wherein the band and the elongated portion have different thicknesses.

19. The endoprosthesis of claim 12, wherein the band and the elongated portion comprise the same composition.

20. The endoprosthesis of claim 12, wherein the elongated portion is bent.

21. An endoprosthesis, comprising a band including a first portion and a second portion, the first portion having a first width and an ASTM E112 G value of about eight or more, and the second portion having a second width different than the first and an ASTM E112 G value of about eight or less, wherein the first and second portions have different grain sizes.

22. The endoprosthesis of claim 21, further comprising an elongated portion extending from the band.

23. The endoprosthesis of claim 22, wherein the elongated portion is bent.

24. The endoprosthesis of claim 22, wherein the band is wider than the elongated portion.

25. The endoprosthesis of claim 21, wherein the first portion has a grain size larger than a grain size of the second portion.

26. The endoprosthesis of claim 21, wherein the first portion has a yield strength lower than a yield strength of the second portion.

27. The endoprosthesis of claim 21, wherein the first and second portions have different thicknesses.

28. The endoprosthesis of claim 21, wherein the first and second portions have different yield strengths.

29. The endoprosthesis of claim 21, wherein the first and second portions comprise a first material selected from the group of stainless steel, a radiopaque element, and an alloy including cobalt and chromium.

30. The endoprosthesis of claim 21, wherein the first portion is wider than the second portion, and the first portion has a grain size larger than a grain size of the second portion.

31. The endoprosthesis of claim 21, wherein the first portion has a yield strength lower than a yield strength of the second portion, and the first width is larger than the second width.

* * * * *